(12) United States Patent
Shores et al.

(10) Patent No.: US 7,984,838 B2
(45) Date of Patent: Jul. 26, 2011

(54) RECYCLED HELIUM GAS SURGICAL INSTRUMENT

(75) Inventors: Rex Wesley Shores, The Colony, TX (US); Gabriel A. Johnston, Trophy Club, TX (US); Robert L. Woods, Arlington, TX (US)

(73) Assignee: Medtronic PS Medical, Inc., Fort Worth, TX (US)

( * ) Notice: Subject to any disclaimer, the term of this patent is extended or adjusted under 35 U.S.C. 154(b) by 467 days.

(21) Appl. No.: 11/417,425

(22) Filed: May 4, 2006

(65) Prior Publication Data

US 2007/0260183 A1  Nov. 8, 2007

(51) Int. Cl.
*F03B 11/04* (2006.01)
(52) U.S. Cl. ............... 227/175.1; 227/156; 173/168; 173/218; 433/103; 433/120
(58) Field of Classification Search ............ 227/175.1, 227/156; 173/168, 218; 433/103, 120
See application file for complete search history.

(56) References Cited

U.S. PATENT DOCUMENTS

| | | | | |
|---|---|---|---|---|
| 3,841,335 | A | | 10/1974 | Tarsitano |
| 4,844,088 | A | * | 7/1989 | Kambin .................. 600/566 |
| 5,160,336 | A | * | 11/1992 | Favre ..................... 606/128 |
| 5,352,230 | A | * | 10/1994 | Hood ....................... 606/99 |
| 5,647,526 | A | * | 7/1997 | Green et al. ............ 227/175.2 |
| 5,906,623 | A | * | 5/1999 | Peterson ................. 606/128 |
| 6,178,755 | B1 | * | 1/2001 | Castellanet .............. 62/50.1 |
| 6,253,575 | B1 | * | 7/2001 | Chludzinski ............. 62/639 |
| 6,471,747 | B1 | * | 10/2002 | Venkatesh et al. ........... 95/90 |
| 6,520,976 | B1 | | 2/2003 | Gage |
| 7,063,247 | B1 | * | 6/2006 | Lund et al. .................. 227/10 |
| 7,186,287 | B2 | * | 3/2007 | Beier ......................... 55/483 |
| 7,335,217 | B2 | * | 2/2008 | Wang et al. ............... 606/171 |
| 7,357,619 | B1 | * | 4/2008 | Del Rio ..................... 415/119 |
| 7,448,525 | B2 | * | 11/2008 | Shelton et al. ........... 227/176.1 |
| 7,598,696 | B2 | * | 10/2009 | McPherson et al. ..... 318/568.18 |
| 7,717,932 | B2 | * | 5/2010 | McFarlin et al. .......... 606/170 |
| 2004/0237789 | A1 | * | 12/2004 | Baksh et al. ................ 96/131 |
| 2005/0245913 | A1 | * | 11/2005 | Del Rio ..................... 606/1 |
| 2005/0256512 | A1 | * | 11/2005 | Del Rio et al. .............. 606/1 |
| 2008/0208265 | A1 | * | 8/2008 | Frazier et al. ............. 606/326 |

FOREIGN PATENT DOCUMENTS

EP  0317507 A1  5/1989

OTHER PUBLICATIONS

European Patent Office, International Searching Authority, Notification of Transmittal of the International Search Report and the Written Opinion of the International Searching Authority or the Declaration, International Application No. PCT/US2007/067892, Oct. 5, 2007, 12 pages.

* cited by examiner

*Primary Examiner* — Rinaldi I. Rada
*Assistant Examiner* — Michelle Lopez
(74) *Attorney, Agent, or Firm* — Haynes and Boone, LLP

(57) ABSTRACT

A system for use in a surgical procedure comprising a pneumatic instrument having an inlet and an outlet, a tank fluidly coupled to the inlet of the pneumatic instrument, wherein the tank provides pressurized helium gas to power the pneumatic instrument, and a compressor fluidly coupled to the outlet of the pneumatic instrument. The compressor receives the helium gas exhausted from the pneumatic instrument and compresses the exhausted helium gas to supply the tank with pressurized helium gas.

21 Claims, 3 Drawing Sheets

RECYCLED HELIUM GAS SURGICAL INSTRUMENT

FIELD OF THE INVENTION

The present disclosure relates generally to pneumatic motors for use in surgical procedures and, more specifically, to a pneumatic surgical instrument that is powered by recycled helium gas within a closed system.

BACKGROUND

Doctors and other medical professionals often use pneumatic powered surgical instruments for dissecting bones and tissue. While various pneumatic powered instruments are known in the art, helium gas has not been used for powering these surgical instruments. Accordingly, there remains a need in the pertinent art to provide a closed system that recycles helium gas to use with pneumatic powered surgical instruments.

SUMMARY

The present disclosure provides a system for use in a surgical procedure. In general, the system utilizes pressurized helium gas to power a pneumatic instrument that is used in a surgical procedure. The system recycles the helium gas exhausted from the surgical instrument and compresses the helium gas so that the pressurized helium gas can be re-used to power the pneumatic instrument. The system may further comprise a controller that uses pressure feedback to maintain a substantially constant pressure level for the helium gas.

The present disclosure also introduces a method for use in a surgical procedure. In general, the method provides a supply of pressurized helium gas to power a pneumatic surgical instrument and recycles the helium gas that is exhausted from the instrument. The recycled helium gas may be filtered and compressed to restore the supply of pressurized helium gas. The method may further regulate the flow of pressurized helium gas going through the surgical instrument.

The present disclosure also provides a kit for use in a medical procedure. In general, the kit comprises a surgical instrument having a pneumatic motor assembly and a supply of pressurized helium gas to power the surgical instrument. The helium gas exhausted from the surgical instrument is pressurized by a remotely located compressor and stored in a remotely located tank for further use.

The foregoing has outlined features of several embodiments so that those skilled in the art may better understand the detailed description that follows. Additional features will be described below that further form the subject of the claims herein. Those skilled in the art should appreciate that they can readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure.

BRIEF DESCRIPTION OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion.

DETAILED DESCRIPTION

Figure 1:
FIG. 1 illustrates a perspective environmental view of a surgical instrument for the dissection of bone and other tissue according to aspects of the present disclosure.

It is to be understood that the following disclosure provides many different embodiments, or examples, for implementing different features of various embodiments. Specific examples of components and arrangements are described below to simplify the present disclosure. These are, of course, merely examples and are not intended to be limiting. In addition, the present disclosure may repeat reference numerals and/or letters in the various examples. This repetition is for the purpose of simplicity and clarity and does not in itself dictate a relationship between the various embodiments and/or configurations discussed. Moreover, the formation of a first feature over, on or coupled to a second feature in the description that follows may include embodiments in which the first and second features are formed in direct contact, and may also include embodiments in which additional features may be formed interposing the first and second features, such that the first and second features may not be in direct contact.

Referring to FIG. 1, illustrated is a perspective environmental view of one embodiment of a surgical instrument 10 for the dissection of bone and other tissue according to aspects of the present disclosure. The surgical instrument 10 is shown operatively associated with a patient A for performing a craniotomy. It will become apparent to those skilled in the art that the described instrument is not limited to any particular surgical application but has utility for various applications in which it is desired to dissect bone or other tissue. Additional applications include:

1. Arthroscopy—Orthopaedic
2. Endoscopic—Gastroenterology, Urology, Soft Tissue
3. Neurosurgery—Cranial, Spine, and Otology
4. Small Bone—Orthopaedic, Oral-Maxiofacial, Ortho-Spine, and Otology
5. Cardio Thoracic—Small Bone Sub-Segment
6. Large Bone—Total Joint and Trauma
7. Dental.

Figure 2:
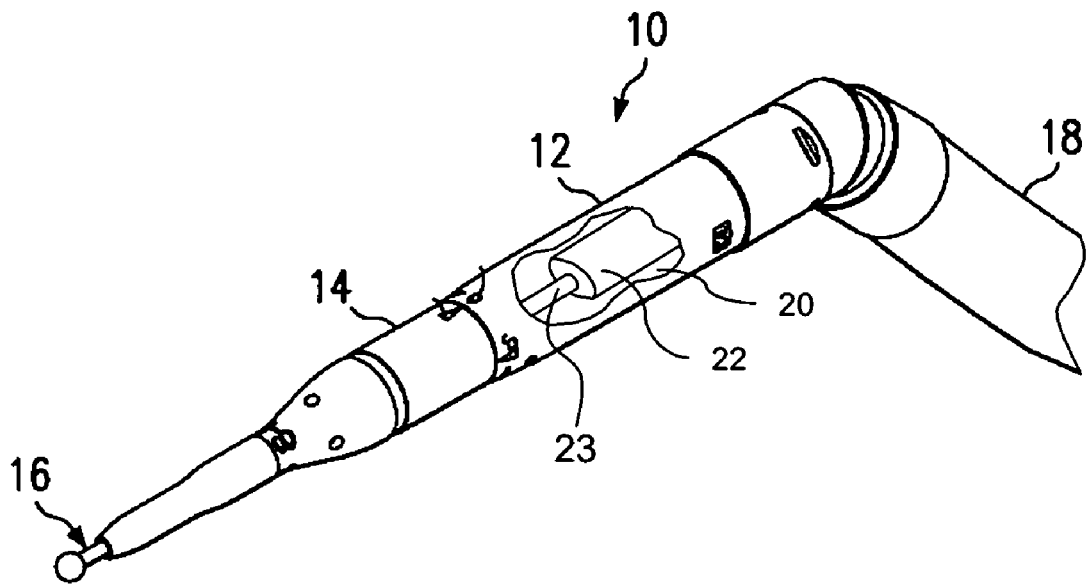
FIG. 2 illustrates a perspective view of the surgical instrument of FIG. 1.

Referring now to FIG. 2, illustrated is a perspective view of one embodiment of the surgical instrument 10 shown in FIG. 1. The surgical instrument 10 is illustrated to generally include a motor assembly 12, an attachment housing 14, a surgical tool 16, and a cylindrical fitting 18. The attachment housing 14 may provide a gripping surface for use by a surgeon and may also shield underlying portions of the instrument 10 during a surgical procedure. In one embodiment, the surgical tool 16 may be a cutting tool or dissection tool, although the type of tool is not essential to implementing the present disclosure.

The attachment housing 14 is adapted and configured to engage the motor assembly 12. The surgical tool 16 may be inserted into attachment housing 14 for engaging with the motor assembly 12. The motor assembly 12 includes an internal cavity 20 adapted and configured to contain a vane motor 22 having a rotor shaft 23. The vane motor 22 may be driven or powered by compressed gas flowing through the cylindrical fitting 18. In general, the rotor shaft 23 of the motor 22 is coupled to the surgical tool 16 such that rotary or linear motion of the rotor shaft 23 may be imparted to the surgical tool 16.

Figure 3:
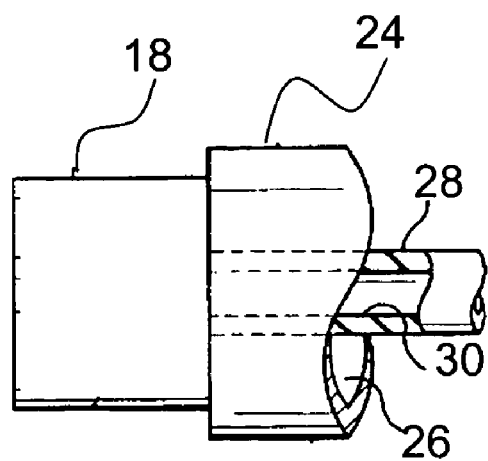
FIG. 3 illustrates an exploded view, partially in cross-section, of part of the surgical instrument of FIG. 2.

Referring also to FIG. 3, illustrated is an exploded view, partially in cross-section, of part of the surgical instrument 10 of FIG. 2. For simplicity and clarity, like components between the two described figures are numbered the same. The cylindrical fitting 18 of the surgical instrument 10 may comprise an inlet for receiving compressed gas to power the motor 22 and an outlet for exhausting the gas out of the instrument. The cylindrical fitting 18 may be affixed to a conduit 24 by means of threading or pinning. Alternatively, the cylindrical fitting 18 may be affixed to the conduit by way of a quick release coupling mechanism.

The conduit 24 may be coaxial having an inner conduit 28 which defines an outer passage 26 and an inner passage 30. The inner passage 30 may be fluidly coupled to the inlet of the cylindrical fitting 18 through which compressed gas is transmitted. The outer passage 26 may be fluidly coupled to the outlet of the cylindrical fitting 18 through which the gas exhausted out from the instrument 10 is transmitted. Another example of a conduit or hose configuration that may be used in the present embodiment is shown in U.S. patent application Ser. No. 10/352,478, filed Jan. 28, 2003, entitled "APPARATUS FOR CONTAINING NOISE GENERATED BY A PNEUMATICALLY POWERED SURGICAL INSTRUMENT AND RELATED METHOD," assigned to the same assignee as the present disclosure, which is hereby incorporated by reference.

In operation, compressed (high pressure) gas may be transmitted through the inner passage 30 of the conduit 24 from a high pressure source (not shown). The vane motor 22 associated with the surgical instrument 10 receives the compressed gas from the inlet of the cylindrical fitting 18. The compressed gas flows through and impacts vanes in the rotor of the motor 22. The force against the vanes causes the rotor shaft 23 of the motor 22 to rotate. The gas may then be exhausted out (low pressure) from the motor 22 through the outlet of the cylindrical fitting 18 and through the outer passage 26 of the conduit 24. The exhausted gas may then be returned to a low pressure source (not shown) to allow the gas to be compressed again for further use.

In order to prevent the gas from escaping the motor assembly 12, the surgical instrument 10 may be sealed by using O-rings or some other type of sealant that is known in the art. Additionally, a foot-operated control valve (not shown) may be incorporated in the conduit 24 so that a surgeon or other individual can actuate the surgical instrument 10 by depressing the valve. Alternative, a hand-operated control valve (not shown) may be implemented in the present embodiment such as the one shown in U.S. Pat. No. 6,520,976, entitled "MODULAR HAND CONTROL FOR PNEUMATIC RESECTING TOOL," assigned to the same assignee as the present disclosure, which is hereby incorporated by reference.

Figure 4:
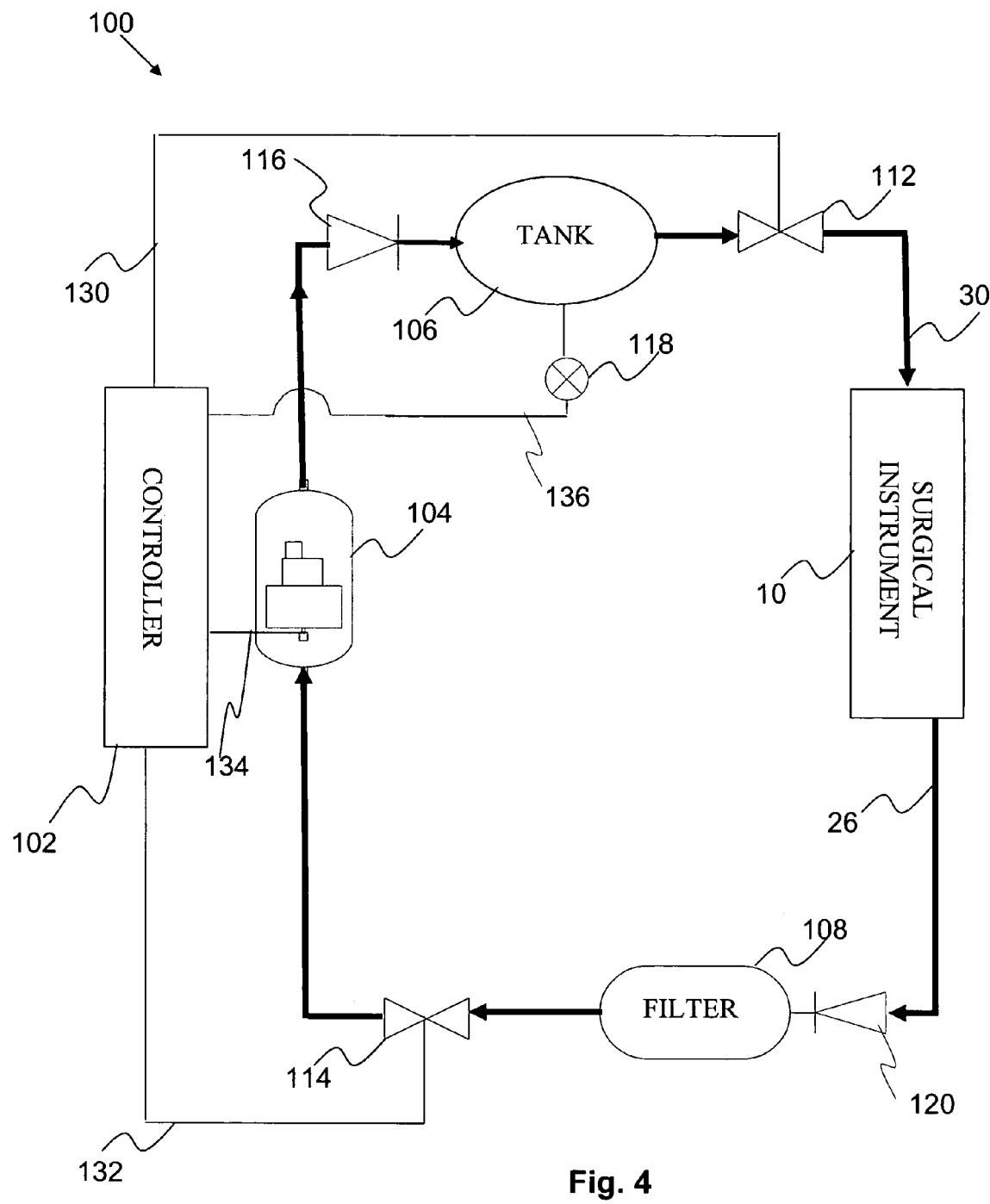
FIG. 4 illustrates a simplified view of one embodiment of a system for use in a surgical procedure according to aspects of the present disclosure.

Referring now to FIG. 4, illustrated is a simplified view of a system 100 for use with the surgical instrument 10 of FIGS. 2 and 3. For simplicity and clarity, like components between the three described figures are numbered the same. In general, the system 100 utilizes helium gas to power the surgical instrument 10. Helium gas may provide equal or better performance than air while only requiring half the driving pressure. Therefore, using helium gas to power the surgical instrument 10 may reduce the physical size of the hand piece and reduce the inlet and outlet hose or conduit diameter. This would make the surgical instrument 10 better suited for surgical procedures because visibility and maneuverability are improved. However, helium gas has not been used due in part to its lack of availability in a hospital setting. The system 100 may be a closed system in that the helium gas is recycled during operation. As a result, the hospital would not be required to maintain large helium gas tanks.

More specifically, the system 100 may comprise a controller 102 for controlling a compressor 104 and control valves 112, 114. The system 100 may also comprise a storage tank 106 for storing a supply of pressurized (compressed) helium gas and a filter 108 for filtering out contaminants that may be carried by the helium gas exhausted out from the surgical instrument 10. The storage tank 106 may be coupled to a pressure gauge 118 that measures a pressure level of the helium gas within the tank. The system 100 may also comprise a check valve 116 fluidly coupled between the compressor 104 and the tank 106 to prevent backflow of the pressurized helium gas to the compressor. It is understood that the components other than the surgical instrument 10 may be remotely located to maintain a sterile environment for the operating room.

In operation, the controller 102 may open the control valve 112 by energizing a control line 130 to allow the supply of pressurized helium gas stored in the tank 106 to flow through the inner passage 30 of the conduit 24 (FIG. 3). The surgeon or other individual may actuate the surgical instrument 10 by depressing the foot-operated or hand-operated control valve (not shown) to allow the pressurized helium gas to flow through the inlet of the cylindrical fitting 18 (FIGS. 2 and 3) thereby powering the instrument. The helium gas may then be exhausted out of the surgical instrument 10 by way of the outlet of the cylindrical fitting 18 and through the outer passage 26 of the conduit 24. The outer passage 26 may be fluidly coupled to the filter 108 so that the exhausted helium gas (low pressure) flows into the filter.

As discussed above, the filter 108 filters out contaminants that may have been generated internally and carried by the exhausted helium gas. The filter 108 may have a disposable filter membrane for easy cleaning when the system 100 is not in operation. Furthermore for maintenance purposes, the filter 108 may have a release valve (not shown) to release pressure that may have built up while the system 100 was in operation. Additionally, the filter 108 may have a check valve 120 that prevents the helium gas from flowing back into the surgical instrument 10.

Continuing with the operation of the system 100, the controller 102 may open the control valve 114 by energizing a control line 132 to allow the filtered helium gas to flow back to the compressor 104. The filtered helium gas may then be compressed (high pressure) to restore the tank 106 with pressurized helium gas and the pressurized helium gas can again be used to power the surgical instrument 10. The controller 102 may turn on the compressor 104 by energizing a control line 134.

In order to maintain a constant pressure level for the helium gas stored in the tank 106, the controller 102 may use pressure feedback 136 which may be provided by the pressure gauge 118. As the surgeon or other individual actuates the surgical instrument 10, the pressure gauge 118 may indicate that the pressure level of the tank 106 has fallen below a required threshold level. The required threshold level may vary depending on the type of application the surgical instrument 10 is used for. As a result, the controller 102 may open the control valve 114 and turn on the compressor 104 to start compressing the helium gas. The compressor 104 restores the tank 106 with pressurized helium gas. When the pressure gauge 118 indicates that the required threshold level has been achieved, the controller 102 may close the control valve 114 and turn off the compressor 104. The check valve 116 prevents any of the pressurized helium gas within the tank 106 from flowing back to the compressor 104.

By using pressure feedback 136, the controller 102 minimizes a runtime of the compressor 104 thereby increasing the efficiency of the system 100. Additionally, the surgical instrument 10 may operate consistently because a constant elevated source pressure for the instrument has been maintained. When the surgeon or other individual is finished, the controller 102 may close the control valves 112, 114 and turn off the compressor 104 by de-energizing the control lines 130, 132, 134. The helium gas is contained within the system 100 for future use. Even though the components within the system 100 are shown as discrete components, it is understood that some components may be combined, such as combining the filter with the compressor.

The various aspects described above are applicable to, or may readily be adapted to, many pneumatic motor applications, including embodiments not explicitly described or illustrated herein. The aspects of the present disclosure are also applicable to motors having any operating speed or range thereof, although the benefits of such aspects will be better recognized at higher operating speeds. The aspects of the present disclosure are also applicable to motors of any size and capable of producing any amount of torque.

Thus, provided is a system for use in a surgical procedure. In one embodiment, the system comprises a pneumatic instrument having an inlet and an outlet, a tank fluidly coupled to the inlet of the pneumatic instrument, wherein the tank provides pressurized helium gas to power the pneumatic instrument, and a compressor fluidly coupled to the outlet of the pneumatic instrument, wherein the compressor receives the helium gas exhausted from the pneumatic instrument and compresses the exhausted helium gas to supply the tank with pressurized helium gas.

In other embodiments, the system also comprises at least one valve for regulating a flow of pressurized helium gas from the tank to the pneumatic instrument and a controller for controlling the compressor and at least one valve. The controller utilizes pressure feedback to maintain a substantially constant pressure for the helium gas contained within the tank. The controller utilizes pressure feedback to minimize runtime of the compressor.

In still other embodiments, the system further comprises a filter for filtering out contaminants in the helium gas exhausted from the pneumatic instrument. The filter may be disposable or cleanable. In other embodiments, the pneumatic instrument comprises a vane motor. In other embodiments, the pneumatic instrument is sealed to prevent the helium gas from escaping. In other embodiments, the system further comprises a conduit having an inner passage and an outer passage, wherein the inner passage is fluidly coupled to the inlet of the pneumatic instrument and the outer passage is fluidly coupled to the outlet of the pneumatic instrument.

The present disclosure also provides a method for use in a surgical procedure. The method comprises providing a supply of pressurized helium gas, driving a pneumatic surgical instrument with the pressurized helium gas, exhausting the helium gas coming from the pneumatic surgical instrument into a compressor, and compressing the exhausted helium gas to restore the supply of pressurized helium gas. In other embodiments, the method further comprises filtering out contaminants in the helium gas exhausted from the pneumatic surgical instrument.

In other embodiments, the method also comprises controlling the compressor to maintain a substantially constant pressure level for the supply of pressurized helium gas, wherein controlling the compressor comprises minimizing runtime of the compressor. In some other embodiments, the method further comprises regulating a flow of pressurized helium gas going through the pneumatic surgical instrument, wherein regulating the flow is performed by at least one valve.

The present disclosure also provides a kit for use in a medical procedure. The kit comprises a surgical instrument having a pneumatic motor assembly and a supply of pressurized helium gas for powering the surgical instrument. The helium gas exhausted from the surgical instrument is recycled and compressed by a compressor to restore the supply of pressurized helium gas. In other embodiments, the kit further comprises a controller for controlling the compressor to maintain a substantially constant pressure level for the supply of pressurized helium gas. In other embodiments, the kit further comprises at least one valve for regulating the flow of pressurized helium gas through the surgical instrument.

In still other embodiments, the kit further comprises a disposable filter for filtering out contaminants in the helium gas exhausted from the surgical instrument. In other embodiments, the supply of pressurized helium gas is stored in a tank. The tank and the compressor are located remotely from the surgical instrument.

The foregoing has outlined features of several embodiments so that those skilled in the art may better understand the detailed description that follows. It is understood that other types of inert gases may also be used which are not readily available in a hospital environment. Those skilled in the art should appreciate that they can readily use the present disclosure as a basis for designing or modifying other processes and structures for carrying out the same purposes and/or achieving the same advantages of the embodiments introduced herein. Those skilled in the art should also realize that such equivalent constructions do not depart from the spirit and scope of the present disclosure, and that they may make various changes, substitutions and alterations herein without departing from the spirit and scope of the present disclosure.

What is claimed is:

1. A system for use in a surgical procedure, the system comprising:
    a pneumatic surgical instrument having an inlet and an outlet;
    a tank fluidly coupled to the inlet of the pneumatic surgical instrument, wherein the tank provides pressurized helium gas to power the pneumatic surgical instrument;
    a compressor fluidly coupled to the outlet of the pneumatic surgical instrument, wherein the compressor receives the helium gas exhausted from the pneumatic surgical instrument and compresses the exhausted helium gas to supply the tank with pressurized helium gas;
    a disposable filter positioned between and fluidly coupled to the outlet of the pneumatic surgical instrument and the compressor, the filter for filtering out contaminants in the helium gas exhausted from the outlet of the pneumatic surgical instrument; and
    a controller for controlling an output of the compressor, the controller having a pressure feedback connection to the tank for maintaining a substantially constant pressure of the helium gas within the tank,
    wherein the pneumatic surgical instrument, tank, compressor, disposable filter, and controller form a closed system in a surgical setting to recycle the pressurized helium gas and to prevent the pressurized helium gas from escaping the closed system.

2. The system of claim 1, further comprises:
at least one valve for regulating a flow of pressurized helium gas from the tank to the pneumatic instrument; and
wherein the controller controls the at least one valve.

3. The system of claim 1, wherein the controller utilizes the pressure feedback connection to the tank to minimize a runtime of the compressor.

4. The system of claim 1, wherein the disposable filter comprises a disposable membrane.

5. The system of claim 1, wherein the pneumatic instrument comprises a vane motor.

6. The system of claim 1, wherein the pneumatic instrument is sealed to prevent the helium gas from escaping.

7. The system of claim 1, further comprising a conduit having an inner passage and an outer passage, wherein the inner passage is fluidly coupled to the inlet of the pneumatic instrument and the outer passage is fluidly coupled to the outlet of the pneumatic instrument.

8. The system of claim 1, wherein the filter further comprises a check valve to prevent the filtered helium gas from flowing back into the outlet of the pneumatic instrument.

9. The system of claim 1, wherein the pressure feedback connection includes a pressure gauge for indicating a pressure level of the tank, and wherein the controller controls a runtime of the compressor based on the pressure level.

10. The system of claim 1, wherein the tank, compressor, disposable, filter, and controller are remotely located to an operating room where the pneumatic surgical instrument is located.

11. A kit for use in a medical procedure, the kit comprising:
a surgical instrument having a pneumatic motor assembly;
a supply of pressurized helium gas for powering the surgical instrument; and
a filter positioned in line between an outlet of the surgical instrument and an input of the supply, the filter sized and shaped to filter out contaminants in the helium gas exhausted from the outlet of the surgical instrument;
wherein the helium gas exhausted from the surgical instrument is recycled through the filter then compressed by a compressor to restore the supply of pressurized helium gas to an inlet of the surgical instrument,
wherein the surgical instrument, the supply of pressurized helium, and the filter are part of a surgical setting.

12. The kit of claim 11, further comprising a controller for controlling the compressor to maintain a substantially constant pressure level for the supply of pressurized helium gas.

13. The kit of claim 11, further comprising at least one valve for regulating the flow of pressurized helium gas from the compressor to the inlet of the surgical instrument.

14. The kit of claim 11, wherein the pneumatic motor assembly is sealed to prevent leakage of the helium gas.

15. The kit of claim 14, wherein the pneumatic motor assembly comprises a vane motor.

16. The kit of claim 11, wherein the filter is a disposable filter.

17. The kit of claim 11, wherein the supply of pressurized helium gas is stored in a tank.

18. The kit of claim 17, wherein the tank and the compressor are located remotely from the surgical instrument.

19. A system for use in a surgical procedure, the system comprising:
a pneumatic surgical instrument for dissecting tissue being powered by a pressurized helium gas, the pneumatic surgical instrument having an inlet for receiving the pressurized helium gas for powering a vane motor of the pneumatic surgical instrument and an outlet for disposing of the pressurized helium gas exhausted by the vane motor;
a helium tank fluidly coupled to the inlet of the pneumatic instrument, wherein the tank provides the pressurized helium gas to power the vane motor of the pneumatic surgical instrument;
a compressor fluidly coupled to the outlet of the pneumatic surgical instrument, wherein the compressor receives the helium gas exhausted from the pneumatic surgical instrument and compresses the exhausted helium gas to supply the tank with pressurized helium gas;
a disposable filter positioned between and fluidly coupled to the outlet of the pneumatic surgical instrument and the compressor, the filter for filtering out contaminants in the helium gas exhausted from the outlet of the pneumatic surgical instrument; and
a controller for controlling an output of the compressor, the controller having a pressure feedback connection to the tank for maintaining a substantially constant pressure of the helium gas within the tank,
wherein the tank, compressor, disposable, filter, and controller are part of a surgical setting, the tank, compressor, disposable, filter, and controller being operable in the surgical setting to provide a constant level of the pressurized helium gas to pneumatic surgical instrument during the surgical procedure,
wherein the pneumatic surgical instrument, helium tank, compressor, disposable filter, and controller form a closed system to recycle the pressurized helium gas and to prevent the pressurized helium gas from escaping the closed system.

20. The system of claim 19, wherein the tank, compressor, disposable, filter, and controller are remotely located to an operating room where the pneumatic surgical instrument is located.

21. The system of claim 19, wherein the pressure feedback connection includes a pressure gauge for indicating a pressure level of the tank, and wherein the controller controls a runtime of the compressor based on the pressure level.

* * * * *